United States Patent
Zhang et al.

(10) Patent No.: US 7,515,970 B2
(45) Date of Patent: Apr. 7, 2009

(54) TRANSEPTAL LEAD

(75) Inventors: Yongxing Zhang, Maple Grove, MN (US); Yunlong Zhang, Mounds View, MN (US)

(73) Assignee: Cardiac Pacemakers, Inc., St. Paul, MN (US)

( * ) Notice: Subject to any disclaimer, the term of this patent is extended or adjusted under 35 U.S.C. 154(b) by 351 days.

(21) Appl. No.: 10/920,695

(22) Filed: Aug. 18, 2004

(65) Prior Publication Data

US 2006/0041300 A1 Feb. 23, 2006

(51) Int. Cl.
*A61N 1/05* (2006.01)
(52) U.S. Cl. .................. 607/126; 607/122; 607/123
(58) Field of Classification Search ............ 607/120, 607/122, 126, 116, 119, 123; 600/375; 604/101.01, 604/101.5
See application file for complete search history.

(56) References Cited

U.S. PATENT DOCUMENTS

| | | | | |
|---|---|---|---|---|
| 4,836,204 A | * | 6/1989 | Landymore et al. | 606/215 |
| 4,940,064 A | * | 7/1990 | Desai | 607/122 |
| 5,190,528 A | | 3/1993 | Fonger et al. | |
| 5,269,319 A | * | 12/1993 | Schulte et al. | 607/123 |
| 5,312,341 A | | 5/1994 | Turi | |
| 5,571,163 A | * | 11/1996 | Helland | 607/123 |
| 5,855,592 A | * | 1/1999 | McGee et al. | 607/4 |
| 5,902,330 A | * | 5/1999 | Ollivier et al. | 607/122 |
| 5,938,660 A | * | 8/1999 | Swartz et al. | 606/45 |
| 5,951,597 A | * | 9/1999 | Westlund et al. | 607/126 |
| 6,014,590 A | | 1/2000 | Whayne et al. | |
| 6,240,322 B1 | | 5/2001 | Peterfeso et al. | |
| 6,296,630 B1 | * | 10/2001 | Altman et al. | 604/508 |
| 6,328,699 B1 | | 12/2001 | Eigler et al. | |
| 6,347,247 B1 | * | 2/2002 | Dev et al. | 607/2 |
| 6,510,348 B2 | * | 1/2003 | Clemens et al. | 607/119 |
| 6,532,378 B2 | * | 3/2003 | Saksena et al. | 600/381 |
| 6,574,514 B2 | | 6/2003 | Partridge et al. | |
| 6,584,362 B1 | | 6/2003 | Scheiner et al. | |
| 7,153,301 B2 | * | 12/2006 | Swartz et al. | 606/41 |
| 2004/0230283 A1 | * | 11/2004 | Prinzen et al. | 607/126 |

OTHER PUBLICATIONS

Spencer, William H., "Atrial Septal Pacing: Synchronising the Atria", *Cardiac Arrhythmias: Pacing & Electrophysiology: The Expert View, Eurospace*;97, Chapter 51,(1998),367-374.

* cited by examiner

*Primary Examiner*—Kennedy J Schaetzle
(74) *Attorney, Agent, or Firm*—Schwegman, Lundberg & Woessner, P.A.

(57) ABSTRACT

A lead includes a lead body and an electrode disposed proximate a distal end of the lead body. A retaining member is disposed proximate the distal end of the lead and adapted to retain the electrode proximate an interatrial septum when the retaining member is located on a left atrial side of the interatrial septum.

30 Claims, 5 Drawing Sheets

TRANSEPTAL LEAD

FIELD OF THE INVENTION

This invention relates to the field of medical leads, and more specifically to an implantable lead.

BACKGROUND

Leads implanted in or about the heart have been used to reverse certain life threatening arrhythmia, or to stimulate contraction of the heart. Electrical energy is applied to the heart via electrodes on the leads to return the heart to normal rhythm.

For example, atrial pacing is accomplished by locating an electrode in the right atrium. However, right atrium pacing and sensing can produce deleterious left heart timing intervals. One technique to apply an energy pulse to the left atrium of the heart is to implant the electrode through the coronary sinus to reach a location below the left atrium. However, it can be difficult to locate the coronary sinus ostium, thus implantation time can be excessive, or the procedure can be unsuccessful. Also, if it desired to apply electrical pulses to both the left atrium and right atrium, two leads may be needed.

SUMMARY

A lead includes a lead body and an electrode disposed proximate a distal end of the lead body. A retaining member is disposed proximate the distal end of the lead and adapted to retain the electrode proximate an interatrial septum when the retaining member is located on a left atrial side of the interatrial septum.

A lead includes a lead body having a shocking electrode disposed proximate a distal end of the lead body. A retaining member is disposed on the lead body and located distally from the shocking electrode. The lead body includes a pre-biased curved section between the shocking electrode and the retaining member.

A method includes inserting a distal tip of a lead through an interatrial septum, deploying a retaining member on the lead on a left atrium side of the interatrial septum such that an electrode on the lead contacts the interatrial septum, and delivering energy pulses to the interatrial septum via the electrode.

DETAILED DESCRIPTION

The following detailed description, reference is made to the accompanying drawings which form a part hereof, and in which is shown by way of illustration specific embodiments in which the invention may be practiced. These embodiments are described in sufficient detail to enable those skilled in the art to practice the invention, and it is to be understood that other embodiments may be utilized and that structural changes may be made without departing from the scope of the present invention. Therefore, the following detailed description is not to be taken in a limiting sense, and the scope of the present invention is defined by the appended claims and their equivalents.

Figure 1:
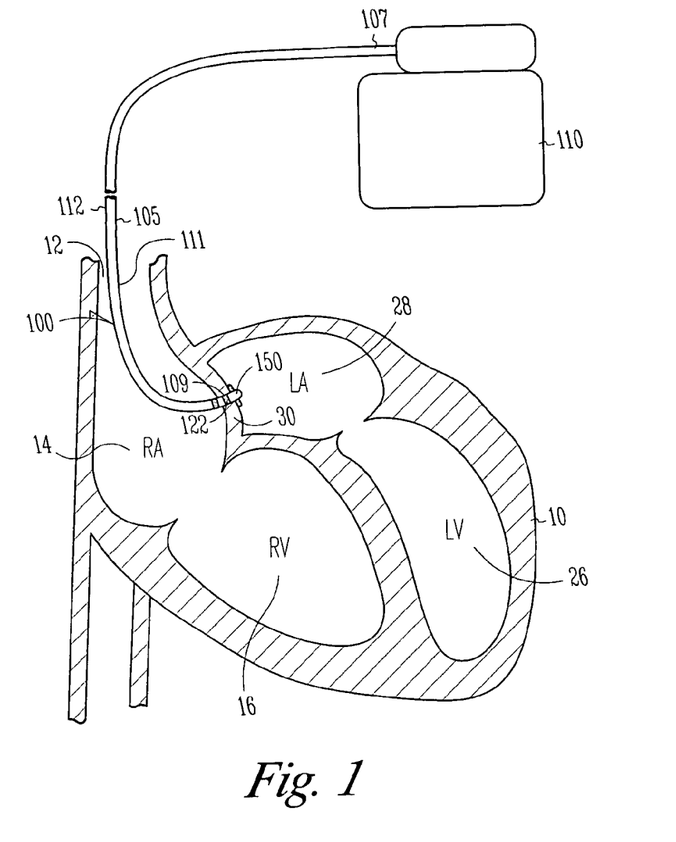
FIG. 1 shows a view of a lead, according to at least one embodiment, implanted within a heart.

FIG. 1 shows a view of a lead 100 implanted within a heart 10. Heart 10 generally includes a superior vena cava 12, a right atrium 14, a right ventricle 16, a left ventricle 26, a left atrium 28, and an interatrial septum 30. In one embodiment, lead 100 is adapted to deliver pacing or defibrillation pulses to heart 10 via an electrode 122. Lead 100 is part of an implantable system including a pulse generator 110, such as a pacemaker or defibrillator.

Pulse generator 110 can be implanted in a surgically-formed pocket in a patient's chest or other desired location. Pulse generator 110 generally includes electronic components to perform signal analysis and processing, and control. Pulse generator 110 can include a power supply such as a battery, a capacitor, and other components housed in a case. The device can include microprocessors to provide processing, evaluation, and to determine and deliver electrical shocks and pulses of different energy levels and timing for defibrillation, cardioversion, and pacing to heart 10 in response to cardiac arrhythmia including fibrillation, tachycardia, and bradycardia.

In one embodiment, lead 100 includes a lead body 105 extending from a proximal end 107 to a distal portion 109 and having an intermediate portion 111. Lead 100 includes one or more conductors, such as coiled conductors, to conduct energy from pulse generator 110 to heart 10, and also to receive signals from the heart. The lead further includes outer insulation 112 to insulate the conductor. The conductors are coupled to one or more electrodes, such as electrode 122. Lead terminal pins are attached to pulse generator 110. The system can include a unipolar system with the case acting as an electrode or a bipolar system.

In one embodiment, lead 100 includes a retaining member 150 disposed on the distal portion 109 of the lead body. As will be further explained below, retaining member 150 is adapted to retain electrode 122 at or near the interatrial septum 30 when the distal end of the lead is mounted to the interatrial septum 30. Since the interatrial septum is so thin (about 3 mm to 5 mm), retaining member 150 provides a technique to hold the lead in position without actively fixating the lead to the thin septum, using a helix, for example. Thus, the lead is easier to implant and the fixation is not as traumatic.

In one embodiment, electrode 122 includes a pacing electrode, such as a ring electrode, adapted for delivering pacing pulses to the left atrium and/or the right atrium of the heart at the interatrial septum 30. For instance, lead 100 can be designed for placement of pacing electrode 122 near or within the interatrial septum 30 to deliver energy pulses which simultaneously affect the left and right atriums. This allows directly pacing and sensing at the left atrium. By locating the electrode at the interatrial septum, the present system can eliminate uncertainties regarding interatrial conduction time. Moreover, by providing simultaneous depolarization of both the left atrium and right atrium it results in decreased incidence of re-entrant AT. In some examples, electrode 122 can be a defibrillation electrode.

In some embodiments, lead 100 can be configured to allow both a stylet or catheter delivery. For example, an opening can be left through the middle of the lead to allow a stylet to be used.

Figure 2:
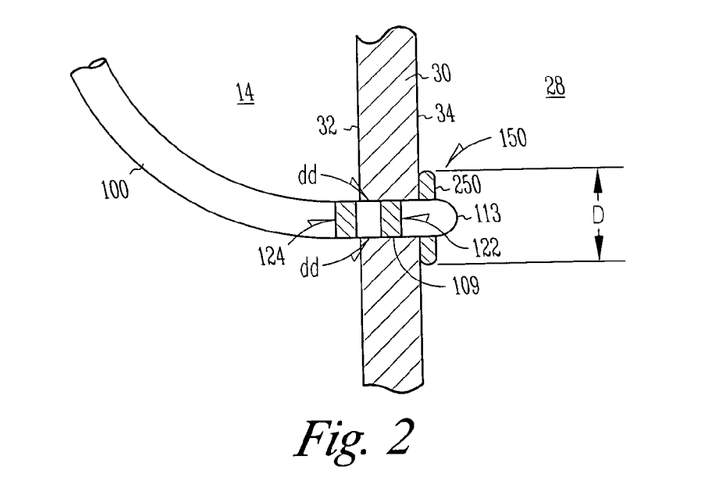
FIG. 2 shows a distal portion of the lead of FIG. 1.

FIG. 2 shows a distal portion of lead 100. In this cross-section view of interatrial septum 30, it is seen that septum 30 includes a first side 32 facing right atrium 14 and a second side 34 facing left atrium 28. In a normal adult, septum 30 is usually between about 3 mm to 5 mm thick.

In one embodiment, retaining member 150 includes an expandable member 250. Expandable member 250 can include a balloon or other structure that has a first orientation where the balloon is relatively flush with the lead body outer surface and is expandable in vivo after a distal end 113 of the lead has past through second side 34 of the interatrial septum. In one embodiment, expandable member 250 can be made of biocompatible material. In some embodiments, expandable member 250 can include a self-expanding structure made from a shape memory material, such as NiTi, for example.

The lead is designed such that after the lead is inserted through septum 30, expandable member 250 is expanded. Expandable member 250 has an outer, cross-section dimension (D) that is larger than the outer diameter (dd) of the distal portion 109 of the lead. Thus member 250 abuts the surface on the left atrium side of the septum to retain the lead and electrode 122 as implanted. Electrode 122 is positioned relative to expandable member 250 such that the electrode is at or within septum 30. Therapy can then be delivered directly to the septum allowing for stimulation of the left atrium and right atrium simultaneously.

In one embodiment, lead 100 includes a second electrode 124 that can be used as a sensing or pacing electrode. Electrode 124 is located proximally from electrode 122 and is located at or near interatrial septum 30 when the lead is implanted. Electrode 124 can be used for sensing cardiac activity near the septum. This information is delivered to the pulse generator and the pulse generator can use the information to deliver therapy pulses to the heart.

Figure 3:
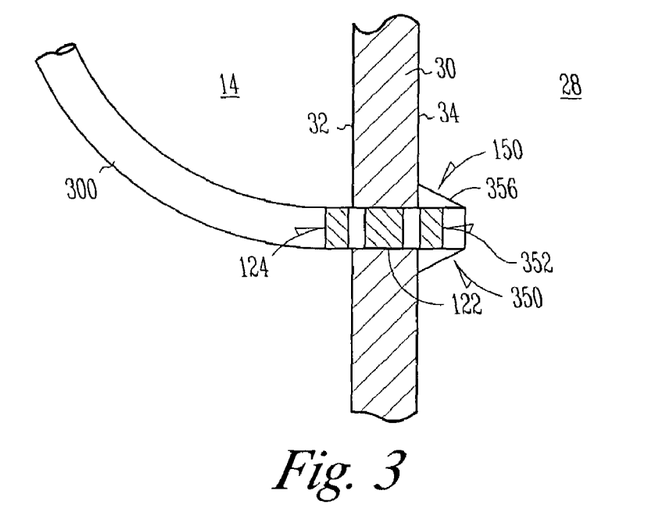
FIG. 3 shows a distal portion of a lead according to at least one embodiment.

FIG. 3 shows a distal portion of a lead 300 according to one embodiment. Lead 300 can include any features of lead 100, or any of the leads discussed below, and the discussions above and below are incorporated herein by reference. Lead 300 includes electrodes 122, 124 and a retaining member 150 including an umbrella structure 350. Umbrella structure 350 includes an expandable structure having a first orientation where one or more tines 356 of the umbrella structure are generally flush against the lead body. The tines 356 can be hinged to the distal end of lead 300 and can be opened by manipulating an actuating suture extending through the lead body to expand the tines into a second, expanded orientation where the outer diameter of the umbrella structure 350 has a greater diameter than the diameter of the distal end of the lead. Again, this holds the lead in position at the interatrial septum. In some examples, tines 356 can be shape memory material or biased members so as to be self-expanding.

In one embodiment, lead 300 (or lead 100 discussed above), can include a drug elution member 352, which can elute steroids, for example, to reduce inflammatory response of the tissue. Member 352 can be located on the distal end of the lead proximate member 150. In one embodiment, member 352 is located distally from electrode 150.

In this example, electrodes 122 and 124 are positioned such that pacing electrode 122 is within and contacting the septum 30 when retaining member 150 is opened on the left atrium side of septum 30, and electrode 124 is at or near the septum.

Figure 4:
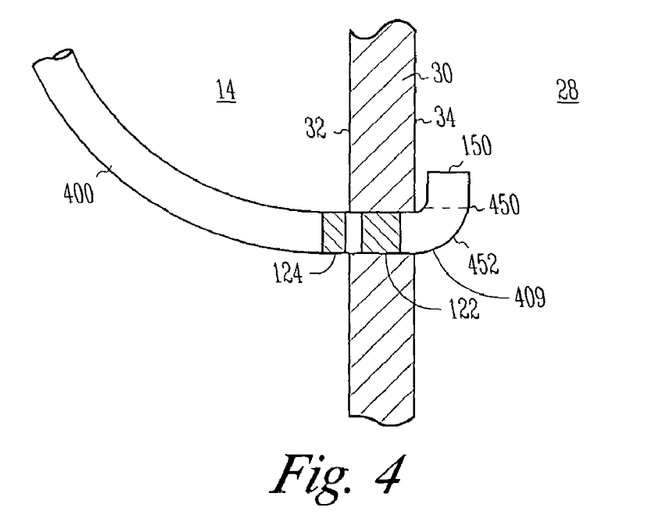
FIG. 4 shows a distal portion of a lead according to at least one embodiment.

FIG. 4 shows a distal portion of a lead 400 according to one embodiment. Lead 400 can include any features of the leads discussed above or below and the discussions are incorporated herein by reference. Lead 400 includes electrodes 122, 124, and a retaining member 150 that includes a pre-biased section 450. For example, pre-biased section 450 can include a pre-formed L-hook or J-hook shape 452 at a distal end 409 of the lead. Pre-biased section 450 is located distally from electrode 122 so that electrode 122 is at or within septum 30 when section 450 is deployed within left atrium 28.

To pre-form section 450 of lead 400, the lead can be manufactured such that it is biased with the shape 452. Thus, the lead naturally reverts to the pre-biased shape when it is implanted. For example, the lead body can be formed in the pre-biased shape or the conductor coils can be formed in the pre-biased shape to bias the lead body into the shape. A stylet or catheter can be used to implant the lead until the distal tip is across septum 30 and within left atrium 28. Then the stylet or catheter is removed and the pre-formed shape 452 returns to its pre-biased shape helping retain the lead in its implanted position, since in its expanded or biased orientation the shape defines an overall outer dimension greater than the dimension of the diameter of the distal end of the lead and thus greater than the hole through the septum.

Figure 5:
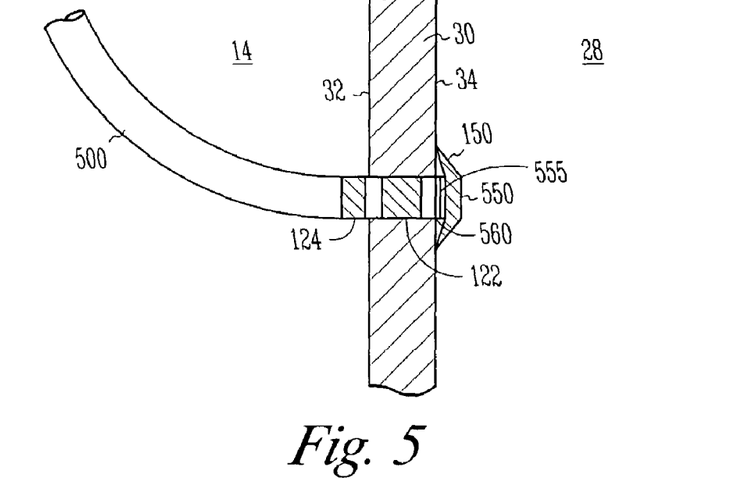
FIG. 5 shows a distal portion of a lead according to at least one embodiment.

FIG. 5 shows a distal portion of a lead 500 according to one embodiment. Lead 500 can include any of the features discussed above or below for other leads described herein. Lead 500 includes electrodes 122 and 124, and a retaining member 150 such as an expandable member 550. In one embodiment, lead 500 includes a sensor 555, which can be a flow sensor or pressure sensor. Sensor 555 can be connected to pulse generator 110 (FIG. 1) through a conductor. In one example, sensor 555 can be a blood flow sensor, such as a metal ring or coil. Such a component has resistance properties such that if a pulse of energy were sent through the component, the component would heat up. This in turn would increase the component's electrical resistance. The electrical resistance could be monitored over time to determine how the resistance changes as the blood flow past it cools it down to blood temperature.

In other embodiments, sensor 555 can be a pressure sensor. In other embodiments, sensor 555 can be a $CO_2$ sensor or an $O_2$ sensor. Sensor 555 can be used to provide pacing ands sensing information to the pulse generator to deliver pulses or modify the settings of the pulse generator.

Lead 500 can also include a radio-opaque marker 560 near the distal tip to help a physician guide the lead when viewed under fluoroscopy.

In use, any of leads described herein can be implanted by inserting the lead through the superior vena cava into the right atrium and then through the interatrial septum. The distal retaining mechanism is deployed once the tip of the lead is into the left atrium. For example, a transeptal sheath catheter with dilator and needle on the tip can be used to perforate the interatrial septum. The catheter is advanced into the left atrium and the dilator is removed. The lead is inserted into the catheter and the distal end is expanded using one of the techniques, as discussed above. The electrode placement can be tested for therapeutic parameters, and the catheter is removed. The electrode 122 is then located at or within the septum and electrode 124 is just proximal from electrode 122. This allows for pacing and sensing of the left atrium, right atrium, or synchronized pacing of the left and right atria. The implantation technique is simpler and easier to do than other techniques to deliver energy pulses to the left atrium. Moreover, the present lead allows for synchronized pacing utilizing a single electrode and the position of the electrode is optimized at the interatrial septum due to the retaining member of the leads.

In some embodiments, the leads discussed herein provide benefits when used for left atrial pacing and sensing. For example, for DDD pacing, the atrial-ventricular (AV) delay interval of the present system can be adjusted to an optimal setting. Also, pacing the left atrium and the right atrium simultaneously can suppress reentrant atrial arrhythmia. Moreover, synchronous depolarization of both the right atrium and left atrium can decrease atrial extrasystoles and interfere with reentrant circuits. The lead allows for optimization of left side timing intervals and can result in an atrial anti-arrhythmic pacing therapy when integrated with certain algorithms, such as, for example, pacing on premature atrial beats.

The present design allows for very little lead presence in the left atrium, thus not requiring special non-thrombogenic material on the lead, although some embodiments can include such material. For example, in one embodiment, at least a portion of one of the leads discussed herein can include an anti-thrombosis coating, such as HYPREN or polyethleneglycol for example. The coating can be placed on the lead body, for example, or on an electrode, on an expandable member, or on other segments of the lead.

Figure 6:
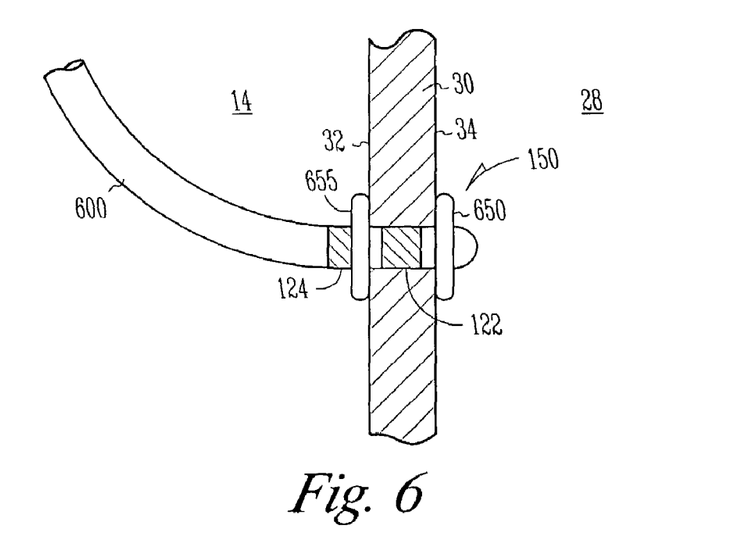
FIG. 6 shows a view of a distal portion of a lead, according to at least one embodiment.

FIG. 6 shows a distal portion of a lead 600 in accordance with one embodiment. Lead 600 can include features of other leads discussed herein. Lead 600 includes electrodes 122, 124, and a retaining member 150, such as expandable member 650, which can be a balloon or other retaining member as discussed above. In one embodiment, lead 600 includes a second retaining member 655 located proximally from retaining member 650. Second retaining member 655 can be an expandable member, such as a balloon, or other retaining member as discussed herein. Second retaining member 655 is located on lead 600 so as to be located on side 32 of interatrial septum 30 when retaining member 650 is on side 34. Thus, the two retaining members sandwich septum 30 between each other. This can help further stabilize electrodes 122, 124.

Figure 7:
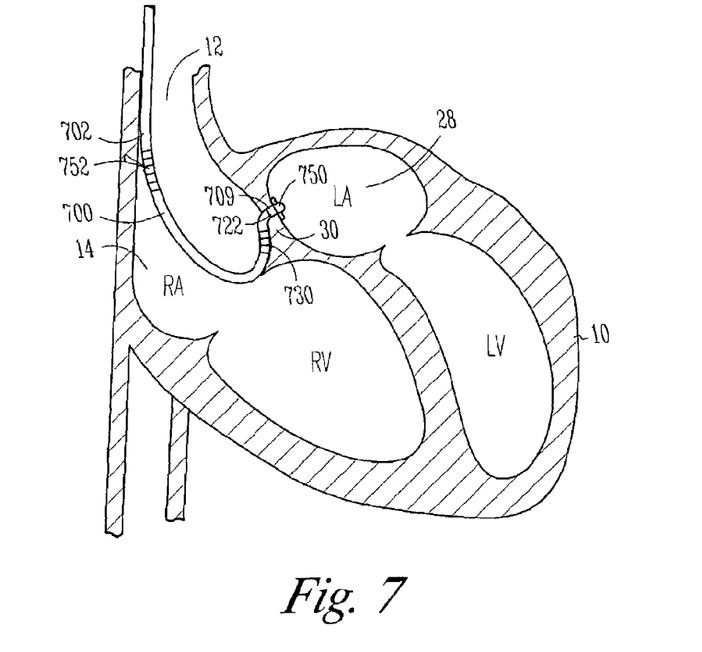
FIG. 7 shows a view of a lead, according to at least one embodiment, implanted within a heart.

FIG. 7 shows a view of a lead 700, according to one embodiment, implanted within heart 10. Lead 700 can include any features as discussed above or below for other leads. Lead 700 is adapted to deliver AF/AT shock treatment via a defibrillation shock electrode 730, which is positioned against the interatrial septum 30. A pacing/sensing electrode 722 can be located on a distal section of the lead and contact the septum. A retaining member 750 is located on a distal end 709 of the lead and adapted to be located within left atrium 28 to hold electrode 730 in position against the septum. This allows the lead to deliver electrical shocks via electrode 730 to the left atrium without requiring the electrode itself to be fixated within the left atrium.

In one embodiment, electrode 730 includes a defibrillation coil electrode adapted for delivering shock pulses to heart 10. Lead 700 can be designed for placement of shock electrode 730 against the septum 30 to deliver shock pulses to the left atrium 28. Electrode 730 can include a shocking coil electrode designed to deliver energy pulses of approximately 0.1 to 50 Joules. By providing direct shocking of the left atrium, the present system can delivery therapy using less energy than if the electrode were located within the coronary sinus, for example.

In one embodiment, lead 700 includes a second shocking electrode 752 which is located on an intermediate portion 702 of the lead so as to be located in the superior vena cava 12 or right atrium 14 when first electrode 730 is against the interatrial septum. In one embodiment, electrode 752 includes a shock electrode adapted for delivering shock pulses to heart 10. Electrode 730 can include a coil electrode designed to deliver energy pulses of approximately 0.1 to 50 Joules. The second shocking electrode 752 minimizes the left atrial shocking energy required so as to help minimize any discomfort of the patient.

In one embodiment, pacing/sensing electrode 722 can include a ring electrode positioned so as to be located near or within interatrial septum 30. Electrode 722 can be used for sensing atrial activity as well as delivering pacing pulses to the left atrium, the right atrium, or synchronized pacing to both atria, such as discussed above.

Figure 8:
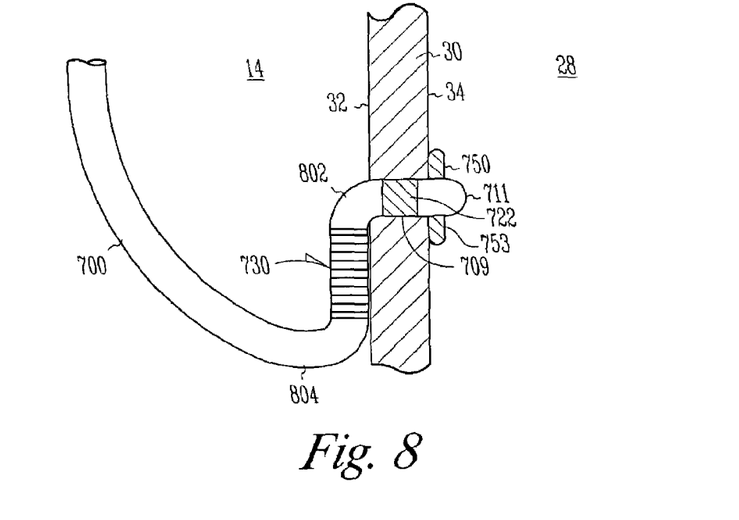
FIG. 8 shows a distal portion of the lead of FIG. 7.
Figure 9:
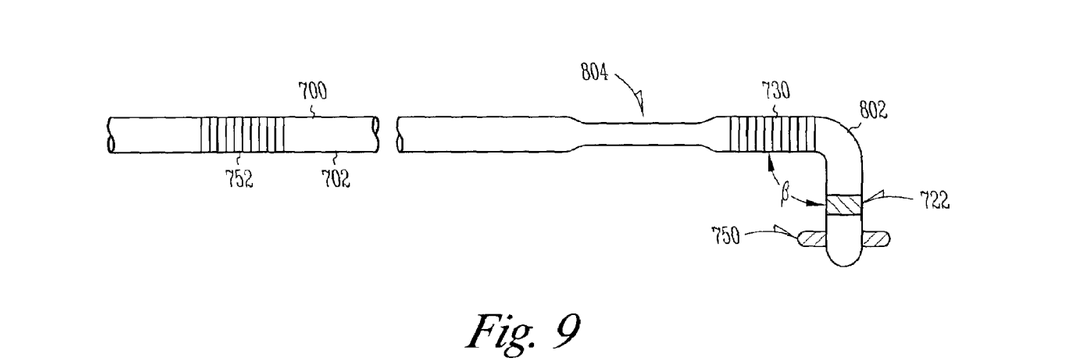
FIG. 9 shows a side view of the lead of FIG. 7.

FIGS. 8 and 9 show further details of lead 700. FIG. 8 shows lead 700 implanted at interatrial septum 30 and FIG. 9 shows a side view of the lead in its unimplanted state. As discussed, lead 700 includes a retaining member 750, such as an expandable balloon 753, on a distal end 709 of the lead body and located distally from electrode 730. In some embodiments, retaining member 750 can include any of the retaining members discussed above, such as an expandable umbrella structure or a pre-formed L-shape or J-shape distal portion section. Retaining member 750 includes an expanded orientation having a larger outer diameter than a diameter of the distal end of the lead body. Accordingly, retaining member 750 holds the lead in place such that shocking electrode 730 abuts against the surface of interatrial septum 30 on the left atrial side 32 of the septum.

In one embodiment, lead 700 includes a less stiff, or more flexible, section 804, which is less stiff than adjacent sections of the lead. Less stiff section 804 is located proximally from electrode 730. This enables electrode 730 to fall naturally against the interatrial septum wall when the lead is implanted since the less stiff section does not provide a biasing counter-force when the electrode is positioned flush against the septal wall. This enhances the electrode stability and contact. Moreover, less stiff section 804 reduces and dampens forces transferred to the site of electrode contact due to motion of the heart against other portions of the lead body.

In one embodiment, less stiff section 804 includes a different, more pliable material than adjacent sections of the lead body. In some embodiments, less stiff section 804 includes a smaller diameter than adjacent sections of the lead body. In some embodiments, less stiff section 804 can be formed by providing a lead wall having a different inner diameter thickness, or by providing a less stiff conductor coil at that location.

In one embodiment, lead 700 includes a pre-biased curved section 802 between shocking electrode 730 and retaining member 750. In some embodiments, pre-biased curved section 802 defines an angle β in the lead body of about 30 degrees to about 120 degrees. In some embodiments, pre-biased curved section 804 defines an angle β in the lead body of about between 85 degrees to about 95 degrees. In some embodiments, pre-biased curved section 804 defines an angle β in the lead body of about 90 degrees. Pre-biased curved section 802 is shaped to force or bias the shocking electrode 730 towards the septum surface so as to abut against the side 32 surface of interatrial septum 30 such that the electrode lies lengthwise against the septal surface when the distal end of the lead extends through the septum in a generally perpendicular direction. This enhances the electrode surface area contact with the surface of the septum. Moreover, the curved section 802 and retaining member 750 act to sandwich the septum between themselves to help hold the lead in place.

As discussed, lead 700 can include a pacing or sensing electrode 722 on the distal end of the lead. In one embodiment, electrode 722 is located between shocking electrode 730 and retaining member 750 so as to be at or within septum 30 when the lead is implanted. Electrode 722 can be used for sensing of cardiac activity and/or for delivering pacing pulses to left atrium 28 or synchronized pacing to the left and right atria.

In some embodiments, lead 700 can include radio-opaque markers near the distal tip to help a physician guide the lead when viewed under fluoroscopy, such as discussed above. In some embodiments, lead 700 can include flow or pressure sensors on a distal end of the lead, such as discussed above for lead 500 (FIG. 5).

In an example use of lead 700, the lead is inserted through the superior vena cava and into the right atrium, using a stylet or catheter delivery. The distal tip of the lead is inserted through the interatrial septum and a retaining member is deployed on the left atrium side of the interatrial septum. The pre-biased curved section of the lead biases the electrode towards the septal surface while the less stiff section does not try to force it away from the surface. Thus the electrode can lie flush against the surface of the septal wall. The lead is coupled to a pulse generator and energy pulses are delivered to the heart. The lead can be used for direct left atrial shocking to treat AF/AT. The direct shock allows the system to decrease shock energy and increase conversion efficacy.

Again, the lead as described above allows for very little lead presence in the left atrium, thus not requiring special non-thrombogenic material on the lead, although some embodiments can include such material. For example, in one embodiment, at least a portion of one of the leads discussed herein can include an anti-thrombosis coating, such as HYPREN or polyethleneglycol for example. The coating can be placed on the lead body, for example, or on an electrode or on other segments of the lead.

It is understood that the above description is intended to be illustrative, and not restrictive. Many other embodiments will be apparent to those of skill in the art upon reviewing the above description. The scope of the invention should, therefore, be determined with reference to the appended claims, along with the full scope of equivalents to which such claims are entitled.

What is claimed is:

1. A lead comprising:
    a lead body extending from a proximal end to a distal end and having an intermediate portion;
    a first electrode disposed proximate the distal end of the lead body;
    a retaining member disposed proximate the distal end of the lead, wherein the retaining member is positioned relative to the first electrode such that the retaining member is configured to retain the first electrode within an interatrial septum when the retaining member is located on a left atrial side of the interatrial septum; and
    a defibrillation shock electrode disposed along the lead proximal from the first electrode and located relative to the retaining member such that the shock electrode is positioned against the interatrial septum when the retaining member is located on the left atrial side of the interatrial septum;
    wherein the lead body further includes a pre-biased curved section located between the retaining member and the defibrillation shock electrode, the pre-biased curved section located and configured to bias the defibrillation shock electrode toward the intratrial septum when the retaining member is located on the left atrial side of the interatrial septum.

2. The lead of claim 1, wherein the first electrode includes a pacing electrode.

3. The lead of claim 1, wherein the first electrode includes a shocking electrode.

4. The lead of claim 1, further including a third electrode disposed proximate the distal end of the lead body.

5. The lead of claim 1, wherein the retaining member includes an expandable balloon.

6. The lead of claim 1, wherein the retaining member includes an expandable umbrella structure.

7. The lead of claim 1, wherein the retaining member includes a pre-formed biased shape at the distal end of the lead body.

8. The lead of claim 1, wherein the retaining member is located distally from the first electrode.

9. The lead of claim 1, further including a radio-opaque marking on the distal end of the lead.

10. The lead of claim 1, further including a sensor located on the distal end of the lead.

11. The lead of claim 1, wherein the retaining member includes an expanded orientation having a larger outer diameter than a diameter of a distal portion of the lead body.

12. The lead of claim 1, wherein the lead includes a drug elution member proximate the distal end.

13. A lead comprising:
    a lead body extending from a proximal portion to a distal portion and having an intermediate portion;
    a first electrode disposed proximate the distal portion of the lead body;
    an expandable retaining member disposed proximate the distal portion of the lead, the retaining member having an expanded orientation having a larger outer diameter than a diameter of the distal portion of the lead body, wherein the expandable retaining member is positioned relative to the first electrode such that the expandable retaining member is configured to position and hold the first electrode within an interatrial septum when the expandable retaining member is located on a left atrial side of the interatrial septum; and
    a defibrillation shock electrode disposed along the lead proximal from the first electrode and located relative to the retaining member such that the shock electrode is positioned against the interatrial septum when the retaining member is located on the left atrial side of the interatrial septum;
    wherein the lead body further includes a pre-biased curved section located between the expandable retaining member and the defibrillation shock electrode, the pre-biased curved section located and configured to bias the defibrillation shock electrode toward the intratrial septum when the retaining member is located on the left atrial side of the interatrial septum.

14. The lead of claim 13, wherein the first electrode includes a pacing electrode.

15. The lead of claim 13, wherein the retaining member includes an expandable balloon.

16. The lead of claim 13, wherein the retaining member includes an expandable umbrella structure.

17. The lead of claim 13, wherein the retaining member includes a pre-formed biased shape at the distal portion of the lead body.

18. The lead of claim 13, wherein the retaining member is located distally from the first electrode such that the retaining member is located on a left atrial side of the interatrial septum when the lead is implanted.

19. A lead comprising:
    a lead body extending from a proximal end to a distal end and having an intermediate portion;
    a shocking electrode disposed proximate the distal end of the lead body; and a retaining member disposed on the lead body and located distally from the shocking electrode, wherein the lead body includes a pre-biased curved section between the shocking electrode and the retaining member, wherein the pre-biased curved section positions the shocking electrode relative to the retaining member such that the shock electrode is biased towards the interatrial septum when the retaining member is located on the left atrial side of the interatrial septum.

20. The lead of claim 19, wherein the lead body further includes a less stiff section located proximally from the shocking electrode.

21. The lead of claim 20, wherein the less stiff section includes a section of the lead body having a smaller diameter than adjacent sections of the lead body.

22. The lead of claim 20, wherein the less stiff section includes a section of the lead body having a more pliable material than adjacent sections of the lead body.

23. The lead of claim 19, wherein the pre-biased curved section is adapted to bias the electrode toward a septal outer surface when the lead is mounted to a septum.

24. The lead of claim 19, wherein the pre-biased curved section defines an angle in the lead body of about 45 degrees to about 120 degrees.

25. The lead of claim 24, wherein the pre-biased curved section defines an angle in the lead body of about between 85 degrees to about 95 degrees.

26. The lead of claim 19, wherein the retaining member includes an expanded orientation having a larger outer diameter than a diameter of a distal portion of the lead body.

27. The lead of claim 19, further including a second shocking electrode disposed along the intermediate portion of the lead body.

28. The lead of claim 19, wherein the shocking electrode is adapted to deliver shocks of energy ranging from approximately 0.1 Joules to approximately 50 Joules.

29. A lead comprising:
a lead body extending from a proximal end to a distal end and having an intermediate Portion;
a first electrode disposed proximate the distal end of the lead body;
a retaining member disposed proximate the distal end of the lead, wherein the retaining member is positioned relative to the first electrode such that the retaining member is configured to retain the first electrode within an interatrial septum when the retaining member is located on a left atrial side of the interatrial septum;
a defibrillation shock electrode disposed along the lead proximal from the first electrode and located relative to the retaining member such that the shock electrode is positioned against the interatrial septum when the retaining member is located on the left atrial side of the interatrial septum; and
a second retaining member disposed on the lead and positioned such that the first electrode is located between the first retaining member and the second retaining member and configured such that the second retaining member is located on the right atrial side of the interatrial septum when the first retaining member is located on the left atrial side of the interatrial septum.

30. A lead comprising:
a lead body extending from a proximal portion to a distal portion and having an intermediate portion;
a first electrode disposed proximate the distal portion of the lead body;
an expandable retaining member disposed proximate the distal portion of the lead, the retaining member having an expanded orientation having a larger outer diameter than a diameter of the distal portion of the lead body, wherein the expandable retaining member is positioned relative to the first electrode such that the expandable retaining member is configured to position and hold the first electrode within an interatrial septum when the expandable retaining member is located on a left atrial side of the interatrial septum; and
a defibrillation shock electrode disposed along the lead proximal from the first electrode and located relative to the retaining member such that the shock electrode is positioned against the interatrial septum when the retaining member is located on the left atrial side of the interatrial septum; and
a second retaining member disposed on the lead and positioned such that the first electrode is located between the first retaining member and the second retaining member and configured such that the second retaining member is located on the right atrial side of the interatrial septum when the first retaining member is located on the left atrial side of the interatrial septum.

* * * * *

UNITED STATES PATENT AND TRADEMARK OFFICE
CERTIFICATE OF CORRECTION

PATENT NO. : 7,515,970 B2  Page 1 of 1
APPLICATION NO. : 10/920695
DATED : April 7, 2009
INVENTOR(S) : Zhang et al.

It is certified that error appears in the above-identified patent and that said Letters Patent is hereby corrected as shown below:

In column 7, line 61, in Claim 1, delete "intratrial" and insert -- interatrial --, therefor.

In column 8, line 47, in Claim 13, delete "intratrial" and insert -- interatrial --, therefor.

In column 9, line 39, in Claim 29, delete "Portion;" and insert -- portion; --, therefor.

Signed and Sealed this

Second Day of June, 2009

JOHN DOLL
*Acting Director of the United States Patent and Trademark Office*